United States Patent
Leminen et al.

(10) Patent No.: US 11,959,034 B2
(45) Date of Patent: Apr. 16, 2024

(54) FLEXIBLE INTEGRATED PRODUCTION PLANT SYSTEM AND METHOD

(71) Applicant: Neste Oyj, Espoo (FI)

(72) Inventors: Anja Leminen, Porvoo (FI); Jukka Hietala, Porvoo (FI); Marja Tiitta, Porvoo (FI); Virpi Rämö, Porvoo (FI)

(73) Assignee: NESTE OYJ, Espoo (FI)

( * ) Notice: Subject to any disclaimer, the term of this patent is extended or adjusted under 35 U.S.C. 154(b) by 50 days.

(21) Appl. No.: 17/787,045

(22) PCT Filed: Dec. 9, 2020

(86) PCT No.: PCT/FI2020/050824
§ 371 (c)(1),
(2) Date: Jun. 17, 2022

(87) PCT Pub. No.: WO2021/123496
PCT Pub. Date: Jun. 24, 2021

(65) Prior Publication Data
US 2023/0096222 A1    Mar. 30, 2023

(30) Foreign Application Priority Data
Dec. 20, 2019   (FI) .................................... 20196122

(51) Int. Cl.
*C10L 1/02* (2006.01)
*C07C 29/60* (2006.01)
(Continued)

(52) U.S. Cl.
CPC ................ *C10L 1/02* (2013.01); *C07C 29/60* (2013.01); *C07C 45/41* (2013.01); *C10G 3/50* (2013.01);
(Continued)

(58) Field of Classification Search
CPC ...... C10L 1/02; C10L 1/04; C10L 2200/0423; C07C 29/60; C07C 45/41; C10G 3/50;
(Continued)

(56) References Cited

U.S. PATENT DOCUMENTS 8,722,924 B1 * 5/2014 Overheul ................ C10L 1/026
560/234
9,884,837 B2    2/2018 Lemp et al.
(Continued)

FOREIGN PATENT DOCUMENTS

EP    1741768 A1    1/2007
EP    2635592 A1    9/2013
(Continued)

OTHER PUBLICATIONS

Finnish Search Report dated Apr. 3, 2020 for Finnish Patent Application No. 20196122. (2 pages).
(Continued)

*Primary Examiner* — Ellen M McAvoy
(74) *Attorney, Agent, or Firm* — BUCHANAN INGERSOLL & ROONEY PC

(57) ABSTRACT

An integrated production plant system includes, at one production site at least two plants of different kinds selected from a renewable paraffinic fuel plant to produce renewable paraffinic fuel in a renewable paraffinic fuel process, a renewable fatty acid alkyl ester (FAAE) fuel plant to produce renewable FAAE fuel in a renewable FAAE process, a renewable base oil plant to produce renewable base oil in a renewable base oil process, and a renewable chemical plant to produce renewable chemical in a renewable chemical process. Each of the processes is provided with a respective renewable feed, where the feed of each of the processes originates from a common renewable system feed, and the feed to at least one of the processes is altered for example by
(Continued)

directing at least part of the feed of at least one of the processes to another of the processes.

22 Claims, 5 Drawing Sheets

(51) Int. Cl.
| | |
|---|---|
| C07C 45/41 | (2006.01) |
| C10G 3/00 | (2006.01) |
| C10L 1/04 | (2006.01) |
| C10M 109/02 | (2006.01) |
| C11C 3/10 | (2006.01) |
| G05B 15/02 | (2006.01) |

(52) U.S. Cl.
CPC ................ C10G 3/60 (2013.01); C10L 1/04 (2013.01); C10M 109/02 (2013.01); C11C 3/10 (2013.01); G05B 15/02 (2013.01); C10G 2300/1014 (2013.01); C10G 2300/1018 (2013.01); C10G 2400/02 (2013.01); C10G 2400/04 (2013.01); C10G 2400/08 (2013.01); C10G 2400/10 (2013.01); C10L 2200/0423 (2013.01); C10L 2200/043 (2013.01); C10L 2200/0446 (2013.01); C10L 2200/0453 (2013.01); C10L 2200/0484 (2013.01); C10L 2290/04 (2013.01); C10L 2290/24 (2013.01)

(58) Field of Classification Search
CPC ............ C10G 3/60; C10G 2300/1014; C10G 2300/1018; C10G 2400/02; C10G 2400/04; C10G 2400/08; C10G 2400/10; C10M 109/02; C11C 3/10; G05B 15/02
See application file for complete search history.

(56) References Cited

U.S. PATENT DOCUMENTS

| | | | |
|---|---|---|---|
| 2010/0043279 A1* | 2/2010 | Abhari | ............... C10L 3/12 44/308 |
| 2010/0146842 A1* | 6/2010 | Dumenil | ............... C12P 7/10 422/600 |
| 2010/0312028 A1 | 12/2010 | Olson et al. | |
| 2010/0317903 A1 | 12/2010 | Knuuttila | |
| 2011/0126448 A1* | 6/2011 | Dumenil | ............... C12P 7/14 435/165 |
| 2011/0258914 A1* | 10/2011 | Banasiak | ............... C10K 1/02 44/605 |
| 2012/0102828 A1 | 5/2012 | Miller | |
| 2013/0110291 A1 | 5/2013 | Carlin et al. | |
| 2013/0340322 A1 | 12/2013 | Knight et al. | |
| 2014/0059921 A1 | 3/2014 | Weaver et al. | |
| 2015/0045594 A1* | 2/2015 | Overheul | ............... C10G 3/42 422/187 |
| 2015/0125913 A1* | 5/2015 | Overheul | ............... C10L 1/02 435/294.1 |
| 2016/0002566 A1* | 1/2016 | Vanhercke | ............... C11C 3/04 |
| 2016/0289576 A1* | 10/2016 | Eilos | ............... C10G 65/00 |
| 2018/0044597 A1 | 2/2018 | Cohen et al. | |
| 2020/0181504 A1* | 6/2020 | Myllyoja | ............... B01J 29/85 |
| 2022/0041939 A1* | 2/2022 | Tiitta | ............... C10G 1/065 |

FOREIGN PATENT DOCUMENTS

| | | |
|---|---|---|
| EP | 2155838 B1 | 9/2014 |
| FI | 100248 B | 10/1997 |
| WO | 2007068795 A1 | 6/2007 |
| WO | 2012059512 A1 | 5/2012 |
| WO | 2012087505 A2 | 6/2012 |
| WO | 2012128840 A2 | 9/2012 |
| WO | 2015061804 A1 | 4/2015 |
| WO | 2016062868 A1 | 4/2016 |
| WO | 2018178130 A1 | 10/2018 |
| WO | 2018234186 A1 | 12/2018 |
| WO | 2018234189 A1 | 12/2018 |

OTHER PUBLICATIONS

International Search Report (PCT/ISA/210) and Written Opinion (PCT/ISA/237) dated Feb. 25, 2021, by the European Patent Office as the International Searching Authority for International Application No. PCT/FI2020/050824. (10 pages).

* cited by examiner

FLEXIBLE INTEGRATED PRODUCTION PLANT SYSTEM AND METHOD

FIELD OF THE INVENTION

The present invention generally relates to producing various bio-based fuels, chemicals, and/or base oils.

BACKGROUND OF THE INVENTION

This section illustrates useful background information without admission of any technique described herein representative of the state of the art.

The production plants used to produce bio-based fuels or chemicals have conventionally been quite inflexible as to required variation in the amount and quality of produced products. The amount and quality of feed has dictated the amount and quality of products obtained, and there has been little means e.g. to cope with the varying demand of manufacturing processes and/or products. A limited shelf-life and/or limited storage capacity of certain products has also caused certain challenges.

Generally concerning feedstocks, from the viewpoint of production profitability, process runnability as well as product yield and quality, an optimal feedstock would have a defined composition, constant quality, good stability, continuous availability, and would preferable be insensitive to storage conditions and time. Typically it is challenging for bio-based feedstocks such as biological fats and oils to meet more than one of these at a time. Furthermore, preferred biological fats and oils for use as feedstocks e.g. in the manufacture of biofuels are usually those of non-edible quality or grade, even waste fast/oils involving further challenges what comes to continuous availability in constant quality and composition. The quality and composition of especially waste fats/oils may be even very poor, and may vary greatly. As the bio-based feedstocks such as fats and oils typically contain fatty acid glycerides, that are materials containing unstable, easily reacting functionalities, their shelf-life is often limited especially if stored for extended periods or kept under suboptimal conditions, such as at elevated temperature. Examples of unstable functionalities present in many glyceridic feedstocks include unsaturated bonds in the carbon chain, prone to form oligomers; ester bonds between the fatty acids and glycerol, susceptible to hydrolysis; and carboxyl and hydroxyl groups that react relatively easily. Furthermore, biological fats and oils, especially of non-edible quality or grade, may contain high amounts of various impurities such as water and metals, the presence of which may accelerate adverse reactions during storage. In addition to chemical instability, especially low-quality or waste fat/oils may be contaminated with microorganisms subjecting these materials to microbial degradation such as hydrolysis of the ester bonds, but also degradation of the carbon chains of the fatty acids may occur. Various pretreatment processes are known for removing impurities that may catalyze side-reactions, and for reducing the amount of reactive functionalities, such as hydrogenation of unsaturated bonds, contributing to improved storage stability. Quality fluctuations could be leveled off by blending off-spec feedstock with on-spec material, so as to obtain a feedstock blend meeting at least the minimum specifications required by the manufacturing process in question. However, these approaches are not fully satisfactory: some of the pretreatments might eliminate functionalities that are actually desired when manufacturing certain bio-based products; certain manufacturing processes may tolerate higher impurity levels than what is needed just for improving storage stability; and leveling off quality fluctuations between feedstock batches by blending involves increased investments in tanks and other blending equipment, and typically also more space is required at the production plant.

SUMMARY

It is an object of certain embodiments of the invention to aid in producing valuable bio-based products such as fuels, base oils and/or chemicals from renewable feedstocks in a flexible manner.

According to a first example aspect of the invention there is provided a method, comprising:
  operating an integrated production plant system comprising, at one production site:
    at least two plants of different kinds selected from:
      a) a renewable paraffinic fuel plant to produce a renewable paraffinic fuel as a main product in a renewable paraffinic fuel process,
      b) a renewable fatty acid alkyl ester (FAAE) fuel plant to produce a renewable FAAE fuel as a main product in a renewable FAAE fuel process,
      c) a renewable base oil plant to produce a renewable base oil as a main product in a renewable base oil process, and
      d) a renewable chemical plant to produce a renewable chemical as a main product in a renewable chemical process; and a storage unit for a common renewable system feed;
    providing each of the renewable processes with a respective renewable process feed, wherein at least part of each renewable process feed originates from a common renewable system feed;
  processing the respective renewable process feed in said renewable process to obtain a respective renewable product flow;
  altering i) the renewable process feed to at least one of the renewable processes by directing at least part of the renewable process feed of at least one of the processes to another of said processes and/or ii) the renewable product flow of at least one of the renewable processes by directing at least part of the renewable product flow of at least one of the processes to another of said processes for use as the respective renewable process feed.

As used herein, "renewable" indicates presence of a material derived from renewable sources. Such renewable material contains a higher number of unstable radiocarbon 14C isotope compared to carbon atoms of fossil origin. Therefore, it is possible to distinguish between carbon compounds derived from renewable or biological sources or raw material and carbon compounds derived from fossil sources or raw material by analysing the ratio of 12C and 14C isotopes. Thus, a particular ratio of said isotopes can be used as a "tag" to identify renewable carbon compounds and differentiate them from non-renewable carbon compounds. The isotope ratio does not change in the course of chemical reactions. Examples of a suitable method for analysing the content of carbon from biological or renewable sources are DIN 51637 (2014), ASTM D6866 (2020) and EN 16640 (2017). As used herein, the content of carbon from biological or renewable sources is expressed as the biogenic carbon content meaning the amount of biogenic carbon in the material as a weight percent of the total carbon (TC) in the material (in accordance with ASTM D6866 (2020) or EN 16640 (2017)).

A biogenic carbon content in a material, which is completely of biological origin, is about 100%. While use of only renewable carbon-containing materials is preferred in the present method, it is to be understood that e.g. some of the minor reactants, such as alkyl alcohols used in the renewable FAAE process or the olefins optionally used in some renewable chemical processes, or certain thermally liquefied recycled organic materials such as pyrolyzed, hydrothermally liquefied, and/or solvothermally liquefied waste plastics, municipal waste and/or end-of-life tires, optionally incorporated in the common system feed and/or in any of the renewable process feeds, may be of fossil origin. The biogenic carbon content of the common renewable system feed, the renewable process feed, and/or the renewable product is lower in cases where other carbonaceous components besides the biological components are used. In the present invention by common renewable system feed, renewable process feed, and renewable product is meant a common renewable system feed, a renewable process feed, and a renewable product having biogenic carbon content of at least 50%, preferably at least 80%, more preferably at least 90%, even more preferably at least 100%.

Expressions olefin and alkene are used interchangeably in this text, and intended to cover all kinds of olefins, including linear olefins, branched olefins, cyclic olefins, diolefins, etc. Exemplary olefins include hydrocarbons such as ethylene, but also olefinic esters, olefinic acids, etc. Terminal olefin refers to an organic compound, where the olefin is positioned at the end of the carbon chain, while internal olefins have a non-terminal carbon-carbon double bond in their carbon chain. Whether the olefin or alkene refers to a compound in the feed or to a product compound is evident from the context, and sometimes the latter is referred to as an olefin product, a terminal olefin product, etc.

In certain embodiments, the common renewable system feed and/or the renewable process feed comprises one or more of fatty and/or resin acids, fatty acid glycerides, such as fatty acid tri-, di- and/or monoglycerides, and thermally liquefied renewable and/or recycled organic materials. Such feeds may be especially susceptible to fluctuations in composition and/or quality depending on the source, and prone to undergoing reactions if stored e.g. for extended periods or at elevated temperature. In certain preferred embodiments, the common renewable system feed comprises at least fatty acid glycerides, such as fatty acid tri-, di- and/or monoglycerides, as these feeds may provide fractions usable as feeds in manufacture of a broader range of renewable products, and particularly fractions usable in all of the following: in a renewable paraffinic fuel process, in a renewable FAAE process, in a renewable base oil process, and in a renewable chemical process, including renewable chemical process involving metathesis of unsaturated compounds, or manufacture of renewable C3-alcohols, such as 1-propanol, 2-propanol, 1,2-propanediol and 1,3-propanediol, by selective hydroprocessing of glycerol.

In certain embodiments, the common renewable system feed and/or the renewable process feed comprises one or more of vegetable oils such as rapeseed oil, canola oil, soybean oil, coconut oil, sunflower oil, palm oil, palm kernel oil, peanut oil, linseed oil, sesame oil, maize oil, poppy seed oil, cottonseed oil, soy oil, tall oil, corn oil, castor oil, jatropha oil, jojoba oil, olive oil, flaxseed oil, camelina oil, safflower oil, babassu oil, seed oil of any of *Brassica* species or subspecies, such as *Brassica carinata* seed oil, *Brassica juncea* seed oil, *Brassica oleracea* seed oil, *Brassica nigra* seed oil, *Brassica napus* seed oil, *Brassica rapa* seed oil, *Brassica hirta* seed oil and *Brassica alba* seed oil, and rice bran oil, or fractions or residues of said vegetable oils such as palm olein, palm stearin, palm fatty acid distillate (PFAD), purified tall oil, tall oil fatty acids, tall oil resin acids, tall oil unsaponifiables, tall oil pitch (TOP), and used cooking oil of vegetable origin; animal fats such as tallow, lard, yellow grease, brown grease, fish fat, poultry fat, and used cooking oil of animal origin; microbial oils, such as algal lipids, fungal lipids and bacterial lipids; and thermally liquefied renewable organic material, such as pyrolyzed, hydrothermally liquefied, and/or solvothermally liquefied solid or fluid biomass, including food waste. The feed may further comprise materials not necessarily renewable such as thermally liquefied recycled organic material, such as pyrolyzed, hydrothermally liquefied, and/or solvothermally liquefied waste plastics and/or end-of-life tires and/or municipal waste. The common renewable system feed and/or the renewable process feed may comprise any combination of said feeds.

In certain embodiments, the respective renewable process feeds originate from the common renewable system feed by being identical to the system feed or by being an intermediate product obtained from the system feed through pretreatment(s) or similar process(es) or by being a combination of the common renewable system feed, as such or as pretreated, and one or more other feeds such as any of the exemplary feeds listed above, as such or as pretreated. In certain embodiments the respective renewable process feed of one or more of the processes may comprise at least part of a renewable product flow of another of said processes.

In certain preferred embodiments the integrated production plant system comprises at least one renewable paraffinic fuel plant. Typically, the renewable paraffinic fuel processes are capable of utilizing/maintaining the carbon chain length of the renewable process feed quite well. This is advantageous as reduced cleavage of the carbon-to-carbon bonds present in the renewable feed materials results in higher yields of valuable high quality liquid paraffins. Additionally, the obtained renewable paraffinic fuels can be used as such or blended in any ratios with respective fossil-based fuels, and typically they have a high market demand, and a reasonable market price. Furthermore, the renewable paraffinic fuel processes may accept side-products or residues from the other renewable processes such as long-chained hydrocarbons from renewable chemical process involving metathesis, as the respective renewable feed thereof. Such side-products or residues would be useless waste in a renewable chemical plant if operated separately, and not as part of the integrated production plant.

In certain preferred embodiments, the integrated production plant system comprises at least one renewable FAAE fuel plant. Typically, also the renewable FAAE fuel processes are capable of utilizing/maintaining the carbon chain length of the renewable process feed well, but the obtained FAAE fuels may have limitations e.g. in blending ratios with fossil-based fuels. Although the renewable FAAE fuel produced in the renewable FAAE fuel plant may be used as a fuel, a part or even all of the produced FAAE may very well be used as renewable process feed in the other renewable processes of the integrated production plant. Thus including at least one renewable FAAE fuel plant in the integrated production plant system provides enhanced flexibility as broadening the feed base, and also the product range of the integrated production plant system. Furthermore, the renewable FAAE process is beneficial also as refining the feed, e.g.

the common renewable system feed, by (trans)esterification into a form that may be more readily usable as the respective renewable process feed in the other renewable processes. For example a renewable chemical process involving metathesis may be sensitive to free fatty acids. Transesterification of a glyceride containing feed may be beneficial also by reducing feed's viscosity, thereby improving its overall handleability, and that may also enhance reaction rate in certain processes, e.g. when using catalysts. Additionally, when needed, the renewable FAAE process may provide various FAAE fuel grades or components including FAAE diesel such as FAME diesel, winter grade FAAE such as unsaturated FAME, and marine grade FAAE a.k.a. bunker fuel, such as C16-FAME.

In certain preferred embodiments the integrated production plant system comprises: at least one renewable paraffinic fuel plant and at least one renewable FAAE fuel plant; or at least one renewable paraffinic fuel plant and at least one renewable chemical plant; or at least one renewable paraffinic fuel plant, at least one renewable FAAE fuel plant and at least one renewable chemical plant; or at least one renewable paraffinic fuel plant, and at least one renewable base oil plant; or at least one renewable paraffinic fuel plant, at least one renewable base oil plant, and at least one renewable FAAE fuel plant; or at least one renewable paraffinic fuel plant, at least one renewable base oil plant and at least one renewable chemical plant; or at least one renewable paraffinic fuel plant, at least one renewable base oil plant, at least one renewable FAAE fuel plant and at least one renewable chemical plant. In preferred embodiments the integrated production plant system comprises at least one renewable paraffinic fuel plant and at least one renewable FAAE fuel plant, allowing manufacture at the same site both separate paraffinic and FAAE fuels but also blends thereof.

In certain preferred embodiments the integrated production plant system comprises at least one renewable paraffinic fuel plant, wherein the renewable paraffinic fuel process of the renewable paraffinic fuel plant comprises hydroprocessing, preferably hydrodeoxygenating and hydroisomerizing, the renewable process feed, and fractionating such as distilling the hydroprocessing effluent to obtain renewable paraffinic fuel as the main product. Exemplary renewable products of the renewable paraffinic fuel process include renewable diesel range hydrocarbons, kerosene range hydrocarbons, gasoline range hydrocarbons, naphtha range hydrocarbons, and gaseous paraffinic hydrocarbons such as butane and propane. Especially when the respective renewable process feed contains fatty acid glycerides, renewable propane is obtainable. Particularly preferred products include diesel range paraffinic hydrocarbons meeting EN 590 requirements for automotive diesel fuel, and kerosene range paraffinic hydrocarbons meeting ASTM D7566-16b, Annex A2, requirements for aviation turbine fuel.

In certain preferred embodiments the integrated production plant system comprises at least one renewable FAAE fuel plant, wherein the renewable FAAE fuel process of the renewable FAAE fuel plant comprises (trans)esterifying a renewable process feed comprising fatty acids and/or fatty acid glycerides in the presence of an alkyl alcohol, preferably C1-C4 alkyl alcohol, more preferably methanol and/or ethanol, and fractionating the (trans)esterification effluent to obtain a renewable FAAE fuel as the main product, preferably biodiesel, bunker fuel, heating oil, and/or lubricant component.

Particularly preferred renewable products include biodiesel fuel blend stocks meeting ASTM D6751-19 standard specification for biodiesel fuel blend stock (B100) for middle distillate fuels.

In certain embodiments the integrated production plant system comprises at least one renewable chemical plant, wherein the renewable chemical process of the renewable chemical plant comprises:

metathesizing a renewable process feed comprising unsaturated fatty acid glycerides and/or unsaturated fatty acid alkyl esters optionally in the presence of an olefin, and fractionating the metathesis effluent to obtain renewable chemicals as the main product, such as terminal olefin products; or subjecting a renewable process feed of crude glycerol to selective hydroprocessing to obtain renewable C3-alcohol, such as 1-propanol, 2-propanol, 1,2-propanediol or 1,3-propanediol.

In certain embodiments producing renewable C3-alcohols, such as 1-propanol, 2-propanol, 1,2-propanediol or 1,3-propanediol, the renewable process feed of crude glycerol is obtained by transesterifying fatty acid glycerides in the presence of an alkyl alcohol to obtain transesterification effluent containing FAAE and crude glycerol, and/or by hydrolyzing fatty acid glycerides to obtain a hydrolysis effluent containing free fatty acids and crude glycerol; and recovering the crude glycerol from the transesterification effluent and/or the hydrolysis effluent.

In certain embodiments, the renewable base oil process of the renewable base oil plant comprises ketonizing a renewable process feed comprising free fatty acids, fatty acid glycerides and/or FAAE, and optionally hydroprocessing, and fractionating the ketonization and/or hydroprocessing effluent to obtain renewable base oil as the main product, preferably meeting API group III specifications for base oils.

In certain embodiments, in addition to said directing to another of said processes, a part of the feed is directed to an alternative product route. An example of such an alternative product route is to take the feed in question out of the integrated production plant system. The feed in question may be used as such, or it may be refined or upgraded elsewhere in a separate process (separate from the processes of the integrated production plant system).

In certain embodiments, the method comprises altering both i) the renewable process feed to at least one of the renewable processes by directing at least part of the renewable process feed of at least one of the processes to another of said processes and ii) the renewable product flow of at least one of the renewable processes by directing at least part of the renewable product flow of at least one of the processes to another of said processes for use as the respective renewable process feed. This may provide enhanced flexibility especially in integrated production plants comprising at least three plants of different kinds, and/or comprising two or more plants of the same kind. Accordingly, whilst in certain embodiments, the production plant system comprises (at least) two plants of different kinds of the said plants of different kinds (the said different kinds being defined in the foregoing), in other embodiments, the production plant system comprises (at least) three plants of different kinds of the said plants of different kinds, and in yet further embodiments, the production plant system comprises all kinds of the said plants of different kinds. And, in any of these embodiments, irrespective of whether the production plant comprises e.g. two, three, or all different kinds of production plants, the production plant system may comprise two or more plants of a same kind.

In certain embodiments of the present method, the altering is performed based on one or more, preferably two or more parameters selected from: inoperability of any of the processes, a target value for the amount of generated carbonaceous waste, a target value for the amount of generated carbon oxide(s), reduced efficiency of a solid catalyst used for processing the renewable process feed in at least one of the processes, increased pressure drop over a fixed catalyst bed used for processing the renewable process feed in at least one of the processes, predetermined target specification for any of the renewable products, predetermined target specification for any of the renewable process feeds, composition of the common renewable system feed, 14C content of the common renewable system feed and/or any of the renewable process feeds and/or renewable products, market price of the renewable products, and market demand of the renewable products.

For example, in certain embodiments, the market demand and/or the market price of the renewable products is such that production of certain renewable products is desirable and production of certain other renewable products is less desirable. The respective renewable feeds of the processes may be altered accordingly.

In certain embodiments, said altering is performed to minimize formation of carbonaceous waste during operating the integrated production plant system. The carbonaceous waste may comprise for example an off-spec renewable product of any of the renewable processes, a side-product of any of the renewable processes, or a renewable process feed not meeting the specification for one or more or any of the renewable processes, or a fraction of any of these. In these embodiments, the common renewable system feed or any of the renewable process feeds may be more efficiently used by directing at least part of the feed of at least one of the processes to another of said processes when a need arises.

In certain embodiments, in which a process operates only partially or is not running at all, wasted feedstock may be eliminated by directing the whole feed or part of the feed of the non-running or partially operating process to one or more of the other processes (other than the non-running or partially operating process).

In certain embodiments, the method comprises:
obtaining information indicating that one of the processes is not running or an amount of a renewable product obtained via that process is to be decreased; and
directing at least part of the renewable feed of that process to another of said processes.

For example, depending on market demand, production of a first renewable product obtainable via a first one of the processes (first process) becomes more preferable compared to production of another renewable product obtainable via a different one of the processes (second process). Accordingly, in order to meet the market demand, at least part of the renewable feed of the second process is directed to the first process (instead of feeding it to the second process).

As another example, it may be that one of the processes is not running, for example, due to maintenance work. Some of the renewable processes, such as the renewable paraffinic fuel process or the renewable base oil process, may use a solid catalyst e.g. for hydroprocessing. Typically solid catalysts have a limited lifetime. Sometimes the decrease in catalyst efficiency over process-running time e.g. in terms of activity and/or selectivity can be estimated, but may be also monitored e.g. based on the composition of the process effluent. Some of the renewable processes may use a solid catalyst arranged in fixed catalyst beds, that may experience plugging e.g. due feed impurities, corrosion products etc., causing an increase in pressure drop over the fixed catalyst bed. When the efficiency of the solid catalyst is expected or measured to become unacceptable, or when unacceptable increase in pressure drop is identified, the renewable process feed of said process may be directed to another of the processes at the production site, until the issue has been resolved, e.g. by regenerating or changing the catalyst.

Yet as another example, the altering may be based on a predetermined target specification for any of the renewable process feeds, and/or the composition of the common renewable system feed, and/or the composition of any of the renewable process feeds. For example, when the amount of unsaturated compounds such as unsaturated fatty acids or their glycerides is reduced in the renewable feed, a renewable product flow fraction comprising unsaturated fatty acid alkyl ester of the renewable FAAE fuel process, being used as the renewable process feed for the renewable chemical process involving metathesis may be directed for example to the renewable paraffinic fuel process and/or to the renewable base oil process for use as renewable process feed therein, and/or collecting said renewable product flow fraction comprising unsaturated fatty acid alkyl ester as FAAE fuel. In another example, when the characteristics of the renewable product flow of any one of the renewable processes change and do not meet a predetermined target specification for said renewable product fully, or in part, the renewable process feed of said renewable process may be directed to another of the renewable processes or said renewable product flow may be directed to another of the renewable processes for use as renewable process feed therein.

In certain embodiments, the integrated production plant system comprises at least a renewable paraffinic fuel plant, a renewable chemical plant and a renewable FAAE fuel plant, and in case the renewable chemical process of the renewable chemical plant is not running the method comprises:
directing a renewable product flow fraction comprising unsaturated FAAE, preferably a C18-FAAE, of the renewable FAAE fuel process, being used as the renewable process feed for the renewable chemical process, to the renewable paraffinic fuel process for use as renewable process feed therein, and/or collecting said renewable product flow fraction as an unsaturated FAAE fuel, preferably as a winter grade FAAE fuel.

In another embodiments the integrated production plant system comprises at least a renewable paraffinic fuel plant, a renewable base oil plant and a renewable FAAE fuel plant, and in case the renewable base oil process of the renewable base oil plant is not running the method comprises:
directing a renewable product flow fraction comprising C16-FAAE of the renewable FAAE fuel process, being used as the renewable process feed for the renewable base oil process, to the renewable paraffinic fuel process for use as renewable process feed therein, and/or collecting said renewable product flow fraction as a FAAE fuel, preferably as a marine grade FAAE fuel.

In certain embodiments, the method further comprises a waste processing system in the integrated production plant system, and passing a carbonaceous waste stream of the integrated production plant system not useful in any of said renewable processes to the waste processing system, and converting it to a conversion effluent comprising carbon oxide(s).

In the present method the carbonaceous waste stream of the integrated production plant system, at least part of the fraction not useful in any of the renewable processes, may be passed to the waste processing system and converted to a conversion effluent comprising carbon oxide(s). Part of the carbonaceous waste stream of the integrated production plant system may find use in some of the renewable processes, or in pretreatment of the common renewable system feed or the renewable process feed. Examples of such uses may include reducing viscosity of more viscous feeds thereby improving e.g. handleability and/or water removal, diluting some feeds thereby reducing their impurity levels or improving temperature control in renewable processes involving exothermic reactions, just to name a few.

The converting may comprise one or more of burning in a flaring unit, burning in a power generation unit e.g. utilizing a super-critical boiler, gasifying in a gasification unit, and reforming in a reforming unit, preferably at least reforming in a reforming unit, to obtain a conversion effluent comprising carbon oxide(s), preferably carbon oxide(s) and hydrogen. Preferably the effluent comprising carbon oxide (s) is not vented, but could be utilized for example for obtaining feed for gas-to-liquid processes (GTL), for generating steam and/or electricity or for compression and injection into the pipelines of the integrated production plant. Electricity generated by burning in the power generation unit could be used for the power demand of the integrated production plant system or fed to electric grid, and syngas obtained from gasifying in the gasification unit could be used especially for manufacturing hydrocarbons by a GTL process such as Fischer-Tropsch. However, preferably the carbonaceous waste stream not useful in any of the renewable processes is converted at least by reforming in a reforming unit, such as by steam reforming or autothermal reforming, to obtain carbon oxides and hydrogen, as the hydrogen may then be reused at the production site e.g. in the renewable paraffinic fuel process, in the renewable base oil process, and/or in the renewable chemical process, when these involve hydroprocessing. Formed carbon oxides could be reused for example in the renewable base oil process. Although some advantageous uses for the carbonaceous waste have been identified, generally it may be preferred to minimize formation of carbonaceous waste, at least the amount of carbonaceous waste not usable in any of the renewable processes. Typically it is more valuable to maintain the existing carbon-carbon bonds present in the renewable material thereby maximizing yield of especially liquid renewable products, than to cleave the carbon-carbon bonds generating gaseous products. In preferred embodiments the altering is performed based on at least a target value for the maximum amount of generated carbonaceous waste, and/or a target value for the maximum amount of generated carbon oxide(s), so as to minimize the amount of the carbonaceous waste.

In various embodiments, the renewable material streams may be optimized, for example, based on demand of the renewable products so that the amount and quality of produced products meet the demand. By controlling the feeds of different processes in the integrated production plant system the produced amount of certain product(s) may be increased and the produced amount of other product(s) decreased as needed, i.e., the ratio of different products may be altered. This aids, for example, in optimizing gained revenue and/or in minimizing or preventing wasted feeds and products.

According to a second example aspect of the invention there is provided an integrated production plant system comprising, at one production site:

at least two plants of different kinds selected from:
a) a renewable paraffinic fuel plant configured to produce a renewable paraffinic fuel as a main product in a renewable paraffinic fuel process,
b) a renewable FAAE fuel plant configured to produce a renewable FAAE fuel as a main product in a renewable FAAE fuel process,
c) a renewable base oil plant configured to produce a renewable base oil as a main product in a renewable base oil process, and
d) a renewable chemical plant configured to produce a renewable chemical as a main product in a renewable chemical process; and
a storage unit configured to receive a common renewable system feed;
wherein the integrated production plant system is configured to:
provide each of the processes with a respective renewable process feed, wherein at least part of each renewable process feed originates from a common renewable system feed;
process the respective renewable process feed in said renewable process to obtain respective renewable product flows;
alter i) the renewable process feed to at least one of the processes by directing at least part of the renewable process feed of at least one of the processes to another of said processes and/or ii) the renewable product flow of at least one of the processes by directing at least part of the renewable product flow of at least one of the processes to another of said processes for use as the respective renewable process feed.

In certain embodiments, the integrated production plant system further comprises a waste processing system configured to convert a carbonaceous waste stream to a conversion effluent comprising carbon oxide(s), wherein the integrated production plant system is further configured to pass a carbonaceous waste stream of the integrated production plant system not useful in any of said renewable processes to the waste processing system, and to convert it to a conversion effluent comprising carbon oxide(s).

In certain embodiments, the waste processing system comprises one or more of a flaring unit, a power generation unit, a gasification unit, and a reforming unit, preferably a reforming unit, such as steam reforming unit and/or a catalytic reforming unit.

In certain embodiments, the integrated production plant system further comprises one or more pretreatment units configured to pretreat at least part of the renewable common system feed and/or of any of the renewable process feeds by one or more of blending, bleaching, degumming, deodorizing, filtering, sedimentation, decanting, centrifuging, evaporating, distillation, heat treating, flocculating, catalytic hydrogenation of unsaturated bonds, treating with an absorbent, and treating with an adsorbent.

In certain embodiments, the integrated production plant system further comprises material flow connections, preferably comprising pipelines, providing fluid communication between the plants, the storage unit, and the optional waste processing system and pretreatment unit(s).

Different non-binding example aspects and embodiments have been presented in the foregoing. The above embodiments and embodiments described later in this description are used to explain selected aspects or steps that may be utilized in implementations of the present invention. It should be appreciated that corresponding embodiments apply to other example aspects as well. Any appropriate combinations of the embodiments can be formed.

BRIEF DESCRIPTION OF THE DRAWINGS

The invention will now be described, by way of example only, with reference to the accompanying drawings, in which.

DETAILED DESCRIPTION

In certain embodiments, an integrated production plant system is provided. The integrated production plant system comprises, at one production site, at least two plants of different kinds selected from: a) a renewable paraffinic fuel plant configured to produce a renewable paraffinic fuel as a main product in a renewable paraffinic fuel process, b) a renewable FAAE fuel plant configured to produce a renewable FAAE fuel as a main product in a renewable FAAE fuel process, c) a renewable base oil plant configured to produce a renewable base oil as a main product in a renewable base oil process, and d) a renewable chemical plant configured to produce a renewable chemical as a main product in a renewable chemical process; and a storage unit configured to receive a common renewable system feed. The integrated production plant system is configured to provide each of the processes with a respective feed, where the feed of each of the processes originates from a common system feed. The integrated production plant system is further configured to provide each of the processes with a respective renewable process feed, wherein at least part of each renewable process feed originates from a common renewable system feed; process the respective renewable process feed in said renewable process to obtain respective renewable product flows; alter i) the renewable process feed to at least one of the processes by directing at least part of the renewable process feed of at least one of the processes to another of said processes and/or ii) the renewable product flow of at least one of the processes by directing at least part of the renewable product flow of at least one of the processes to another of said processes for use as the respective renewable process feed.

For this purpose, the integrated production plant system may comprise material flow connections, preferably comprising pipelines, providing fluid communication between the plants, the storage unit, and the optional waste processing system and pretreatment unit(s). The material flow connections may also be arranged, at least in part, by trucks etc.

Figure 1:
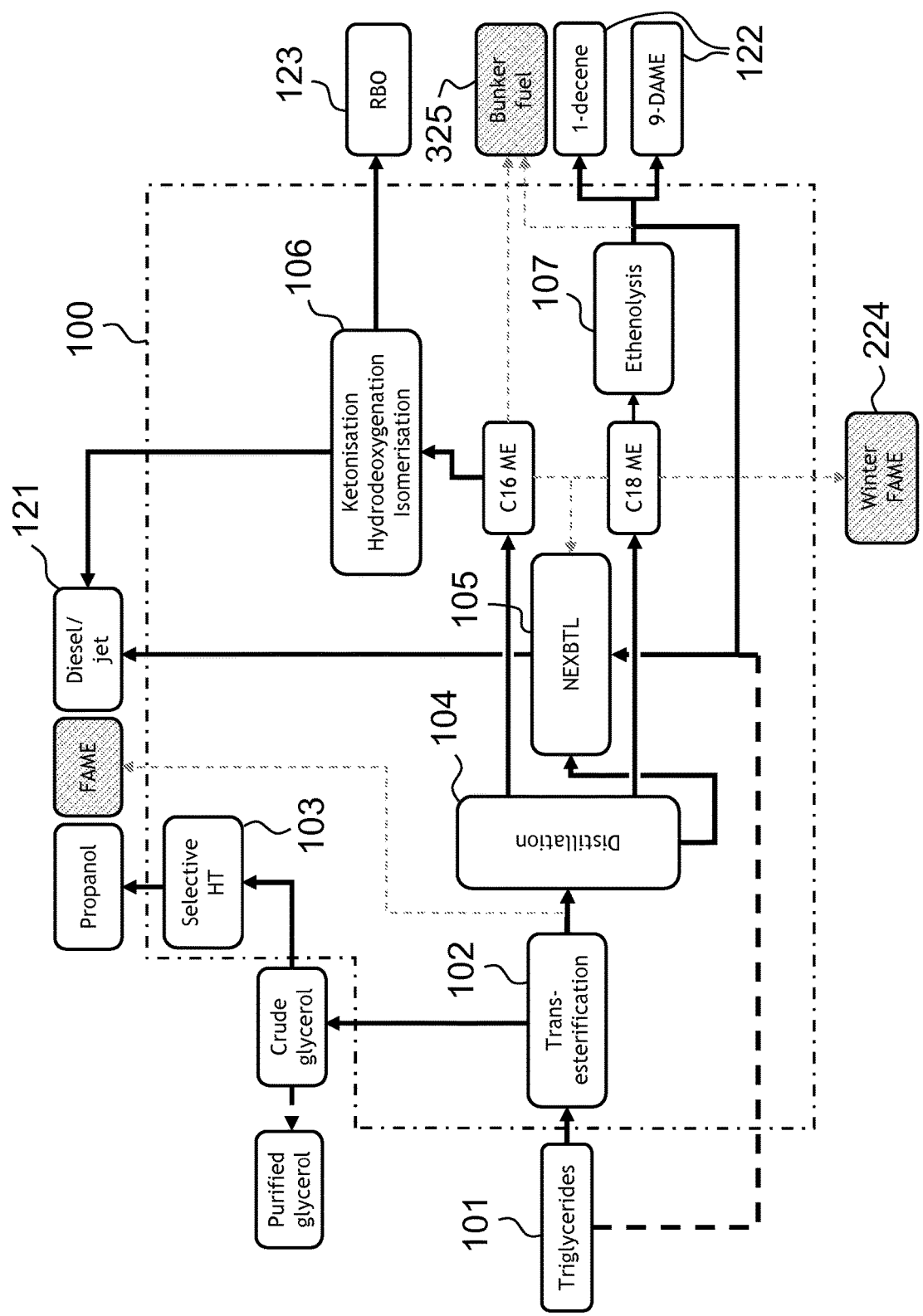
FIG. 1 shows a processing scheme for producing various renewable chemicals in accordance with certain embodiments.

FIG. 1 shows an example of a processing scheme for producing various renewable chemicals in accordance with certain embodiments in an integrated production plant system 100. Here, triglycerides are selected as the representative feedstock. Crude glycerol is produced during a transesterification process 102 from triglycerides 101. Crude glycerol may be purified to obtain purified glycerol, and/or directed to a renewable chemical process for producing renewable C3-alcohol, such as 1-propanol, 2-propanol, 1,2-propanediol or 1,3-propanediol, in a selective hydrotreatment (HT)/hydroprocessing 103.

The transesterification process 102 conducted in the presence of methanol produces fatty acid methyl esters (FAME). FAME may be used as such as indicated by the dotted line in FIG. 1, but more preferably at least a major portion of FAME is entered a fractionating distillation process 104. Fatty acid esters containing fractions are separated according to the chain length of the fatty acid esters.

C16 methyl ester fraction is recovered in the distillation process 104 and is used as a feed for a process 106 comprising ketonisation, hydrodeoxygenation, and isomeration (referred to as the renewable base oil process 106). The process 106 produces renewable base oil (RBO) 123 but also diesel fuel and/or jet (aviation) fuel components 121.

Further, C18 methyl ester fraction is recovered in the distillation process 104 and is directed to an ethenolysis process 107 (referred to as another renewable chemical process 107) to produce renewable chemicals (other than renewable C3-alcohol), such as 1-decene and 9-decenoic acid methyl ester (9-DAME), e.g., for lubricant and surfactant products.

Further distillation products are used as a feed for a process 105 comprising hydroprocessing, such as hydrodeoxygenation and isomeration (referred to as paraffinic fuel process 105, NEXBTL) to produce renewable gasoline, diesel fuel and/or jet fuel components 121. Products obtained from the ethenolysis 107 may also be used as a feed for the process 105.

FIG. 1 shows further material flow routes, indicated by dotted lines, not in use in the processing scheme of FIG. 1. These include using the C16 methyl ester fraction as a feed for the process 105, using the C18 methyl ester fraction as a feed for the process 105, using the C16 methyl ester fraction as a component of bunker fuel 325, using products obtained from the ethenolysis 107 as bunker fuel components 325, and upgrading the C18 methyl ester fraction for winter FAME products.

Instead of undergoing transesterification, the triglyceridic feedstock may be used directly as a feed for the process 105.

The various processes disclosed in the preceding are performed at various plants of the integrated production plant system. For example, the selective hydroprocessing 103 to produce renewable C3-alcohol (propanol) occurs at a renewable chemical (propanol) plant. The process 105 occurs at a renewable paraffinic fuel plant. The process 106 occurs at a renewable base oil plant. And, the process 107 occurs at said another renewable chemical plant. As shown in FIG. 1, there are provided material flow connections (or routes) between the plants. Using the connections, the feeds of different processes in the integrated system may be altered (a feed normally used in one of the processed may be reverted wholly or partially to another of the processes). In certain embodiments, the produced amount of certain product(s) is increased and the produced amount of other product(s) decreased as needed, i.e., the ratio of different products is altered. This aids, for example, in optimizing gained revenue and/or in minimizing or preventing wasted materials.

The processing scheme shown in FIG. 1 may face exceptional circumstances as the case may be. For example, one of the processes shown may not be running due to maintenance or otherwise. The following embodiments show methods of coping with such exceptional circumstances.

Figure 2:
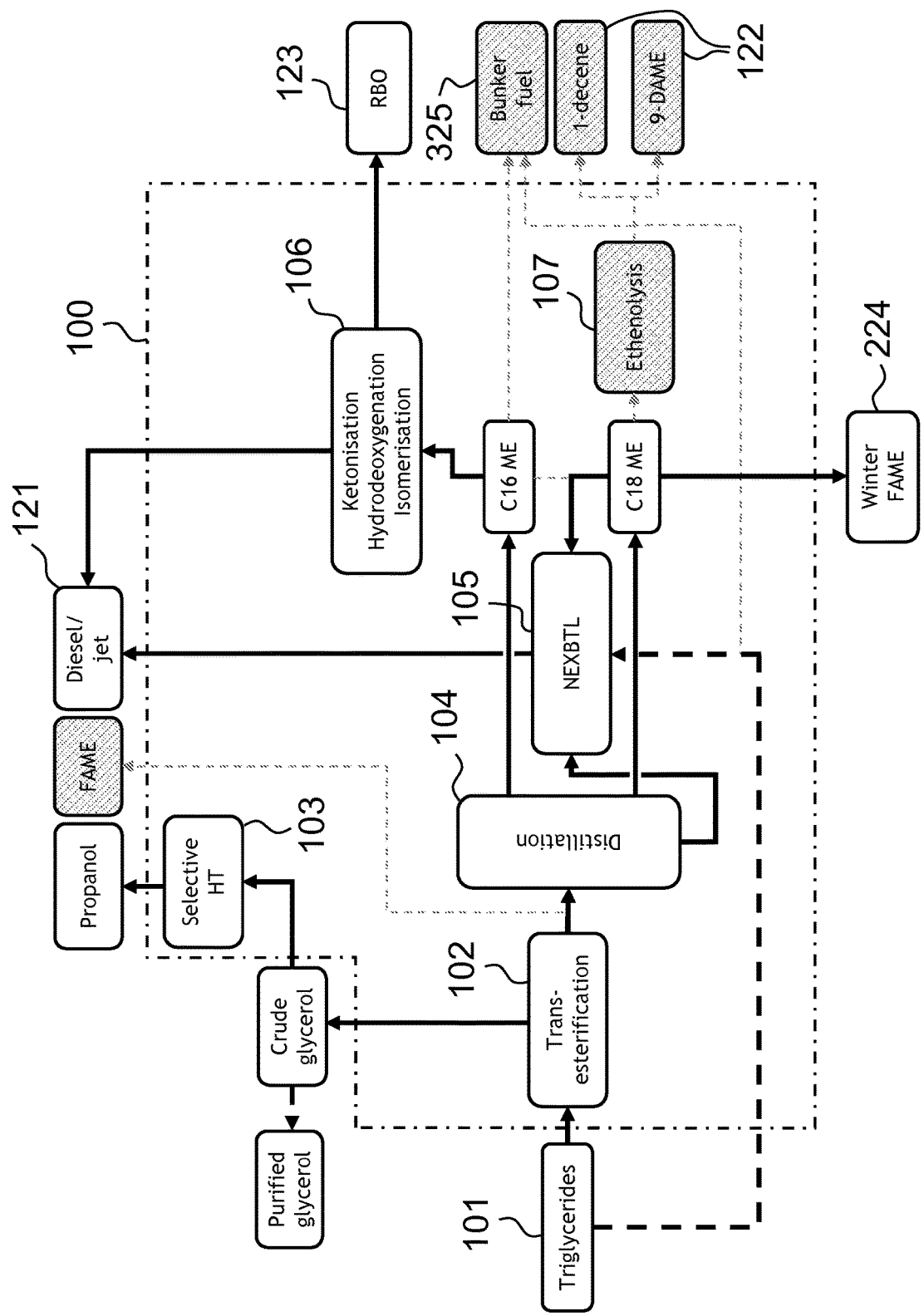
FIG. 2 shows a first exceptional circumstance in accordance with certain embodiments.

FIG. 2 shows a first exceptional circumstance in accordance with certain embodiments. In this case the ethenolysis 107 is not running. As the other processes operate as intended, the C18 methyl ester fraction normally used as a feed for the ethenolysis 107 remains unused. As a solution, in certain embodiments, the remaining C18 methyl ester fraction is used as a feed for the process 105. In other embodiments, the remaining C18 methyl ester fraction is upgraded for winter FAME products. In yet other embodiments, a certain percentage of the remaining C18 methyl ester fraction is upgraded for winter FAME products and a remaining portion is used as a feed for the process 105.

Figure 3:
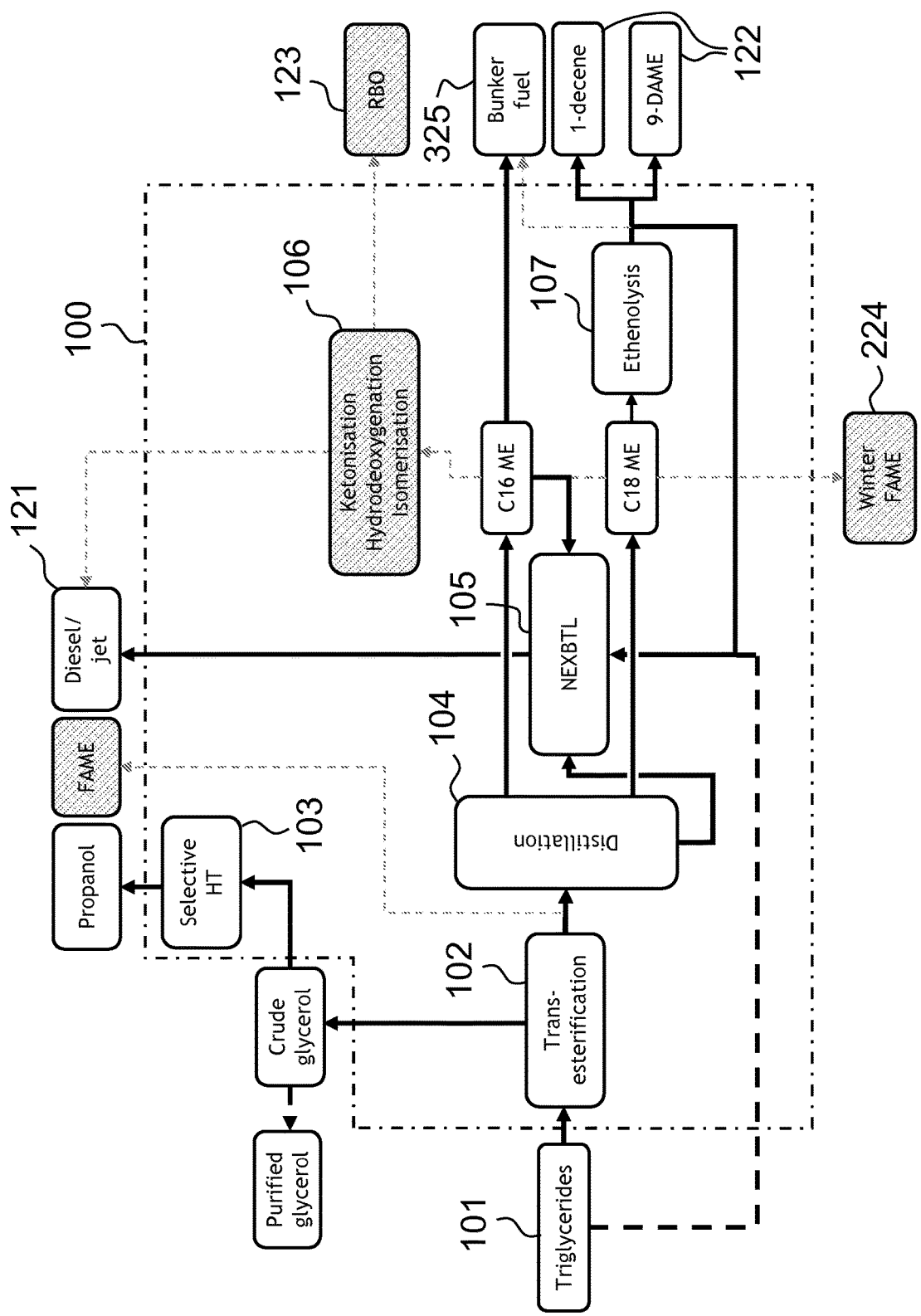
FIG. 3 shows a second exceptional circumstance in accordance with certain embodiments.

FIG. 3 shows a second exceptional circumstance in accordance with certain embodiments. In this case the renewable base oil process 106 (e.g., its ketonisation part) is not running. As the other processes operate as intended, the C16 methyl ester fraction normally used as a feed for the process 106 remains unused. As a solution, in certain embodiments, the remaining C16 methyl ester fraction is used as a feed for the process 105. In other embodiments, the remaining C16 methyl ester fraction is used as a component of bunker fuel 325. In yet other embodiments, a certain percentage of the remaining C16 methyl ester fraction is used as a feed for the process 105 and a remaining portion is used as a component of bunker fuel 325.

Figure 4:
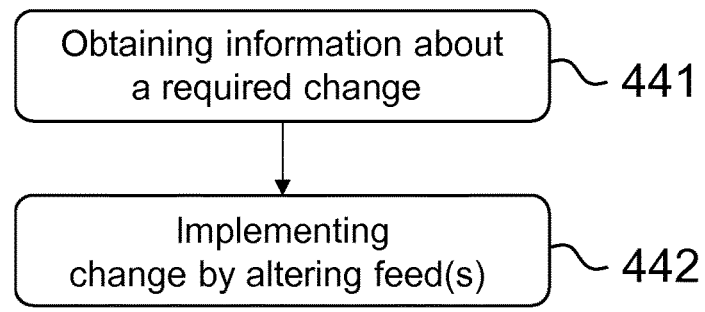
FIG. 4 shows a flow chart of a method in accordance with certain embodiments.

FIG. 4 shows a flow chart of a method in accordance with certain embodiments. In step 441, information about a required change is obtained. In step 442, the change is implemented by altering the feed(s) to the various processes as needed.

The information of the required change in embodiments is obtained by obtaining a parameter that is indicative of at least one of the following: inoperability of a process, wasted feed in one or more of the processes, market price of different products, and market demand of different products.

Figure 5:
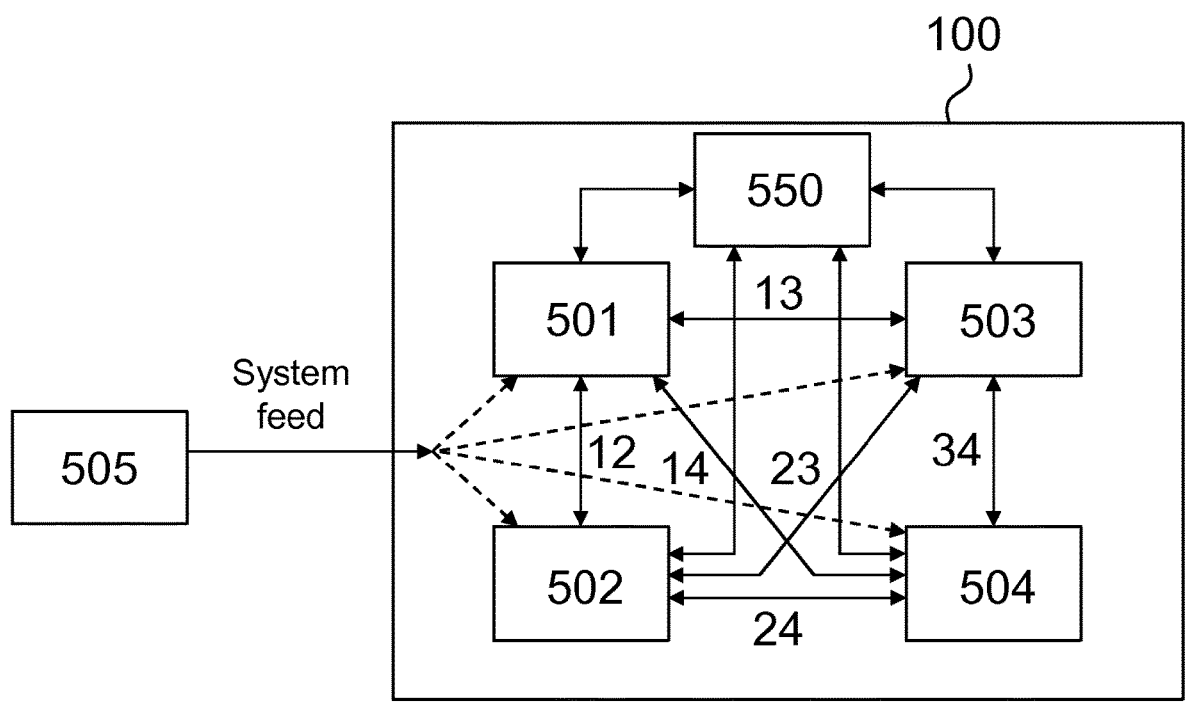
FIG. 5 shows an exemplary schematic view of an integrated production plant system in accordance with certain embodiments.
Figure 6:
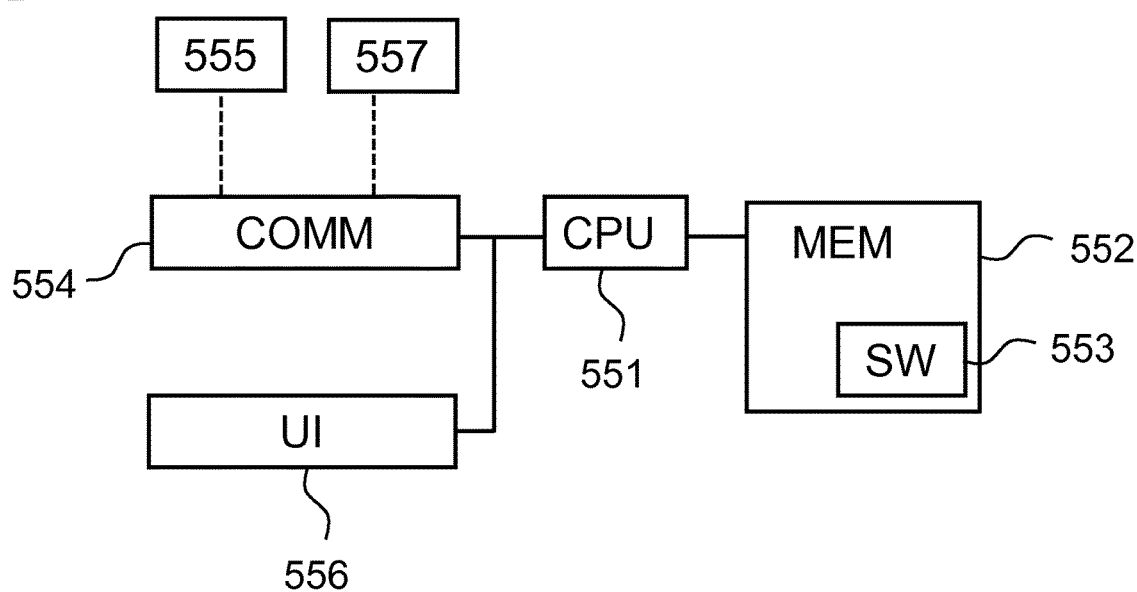
FIG. 6 shows a control system in accordance with certain embodiments.

FIG. 5 shows an exemplary schematic view of the integrated production plant system 100 in accordance with certain embodiments. A renewable chemical (e.g. C3-alcohol) plant 501, renewable FAAE fuel plant 102, renewable base oil plant 103, and another renewable chemical plant 504 receive respective feeds originated from a common renewable system feed as depicted by dotted arrows, wherein reference numeral 505 depicts a storage unit for the system feed. The arrows 12-14, 23, 24, and 34 depict material flow connections between the various plants (although in a real scenario all connections might not be implemented). A computer-controlled process control system 550 controls the operation of the plants 501-504. The control system 550, as shown in FIG. 6, comprises at least one processor 551 to control the operation of the system 100 and at least one memory 552 comprising a computer program or software 553. The software 553 includes instructions or a program code to be executed by the at least one processor 551 to control the system 100. The software 553 may typically comprise an operating system and different applications.

The control system 550 further comprises at least one communication unit 554. The communication unit provides for an interface for internal communication of the system 100. In certain embodiments, the control system 550 uses the communication unit 554 to send instructions or commands to and to receive data from different parts of the system 100 such as sensor or measurement units 555 which may provide input parameters for the control system 550 to make decisions leading to said altering of the renewable process feed and/or the renewable product flow. Further, the control system 550 in certain embodiments uses the communication unit 554 to control process flow or product flow adjustment units 557 which may include valves and different controllers, such as mass flow controllers, to implement the desired alterations as decided.

The control system 550 may further comprise a user interface 556 to co-operate with a user, for example, to receive input such as process parameters or commands from the user.

As to the operation of the system 100, the control system 550 controls the altering of the respective feeds of the processes in the way disclosed in the preceding. In certain embodiments, the system 100 is configured, by means of being programmed, for example, to alter the feed to at least one of the processes by directing at least part of the feed of at least one of the processes to another of said processes.

Renewable Feed

Depending on the specific renewable paraffinic fuel process, renewable FAAE fuel process, renewable base oil process and the renewable chemical process, the respective process feeds may have different preferred specifications. For example, when the renewable chemical process is a metathesis process, it is essential that the respective renewable process feed contains compounds having at least one carbon-carbon double bond, such as unsaturated fatty acids. Typically, the respective renewable process feed of metathesis process comprises C18:1 fatty acids. Good feeds for said process include seed oils, such as sunflower oil, as these are rich in unsaturated fatty acid glycerides. On the other hand, particularly suitable glyceride containing feedstocks for renewable base oil production, are those which comprise palmitic acid, i.e. C16 fatty acids. When the renewable chemical process involves manufacture of C3-alcohol, such as 1-propanol, 2-propanol, 1,2-propanediol or 1,3-propanediol, by selective hydroprocessing, it is essential that the respective renewable process feed contains crude glycerol, obtainable e.g. by hydrolyzing or transesterifying fatty acid glycerides. Furthermore, when it is desired to obtain renewable propane from the renewable paraffinic fuel process, glyceride-containing renewable process feed is preferred.

Table 1 lists availability of some C16 and C18 free fatty acids from natural material sources, and the fatty acid carbon chain lengths and unsaturation of exemplary fats and oils found in the literature, possibly suitable for use in the method of the present invention.

TABLE 1

Exemplary free fatty acid and glyceride containing feedstocks usable in the present invention.

| Fat/oil | \multicolumn{13}{c}{The fatty acid distribution of glyceride containing feedstocks usable in the present invention (%-wt)} | Amount of FFAs [2]Amount of C16 and C18 FFAs |
|---|---|---|---|---|---|---|---|---|---|---|---|---|---|---|
| | 8:0 | 10:0 | 12:0 | 14:0 | 16:0 | 18:0 | 18:1 | 18:2 | 18:3 | 20:0 | 20:1 | 22:0 | 22:1 | |
| Canola | | | | 0.1 | 4.1 | 1.8 | 60.9 | 21.0 | | 0.7 | | 0.3 | | |
| Crude tall oil | | | | | [1]1-2 | | | | | | | | | |
| Cottonseed | | | 0.7 | | 21.6 | 2.6 | 18.6 | 54.4 | 0.7 | 0.3 | | 0.2 | | |
| Crumbe | | | | | 1.7 | 0.8 | 16.1 | 8.2 | 2.9 | 3.3 | | 2.2 | 59.5 | |
| Cuphea (PSR-23) | 0.8 | 81.9 | 3.2 | 4.3 | 3.7 | 0.3 | 3.6 | 2.0 | 0.3 | | | | | |
| Jatropha | | | | | [1]15 | | | | | | | | | 1.5-5 |
| Palm | | | 0.2 | 1.1 | 44.0 | 4.5 | 39.1 | 10.1 | 0.4 | 0.4 | | | | 4-7 |
| Palm Kernel | 3.3 | 3.4 | 48.2 | 16.2 | 8.4 | 2.5 | 15.3 | 2.3 | | 0.1 | 0.1 | | | |
| Palm stearin | | | | | [1]60 | | | | | | | | | 0.1 |
| PFAD | | | | | [1]45 | | | | | | | | | 75-88 |
| Rapeseed | | | | | 2.7 | 1.1 | 14.9 | 10.1 | 5.1 | 10.9 | | 0.7 | 49.8 | |
| Soybean | | | 0.1 | 0.2 | 10.7 | 3.9 | 22.8 | 50.8 | 6.8 | 0.2 | | | | 2.5 |
| Sunflower | | | | | 3.7 | 5.4 | 81.3 | 9.0 | | 0.4 | | | | 0.5 |
| Lard | | 0.1 | 0.1 | 1.5 | 26.0 | 13.5 | 43.9 | 9.5 | 0.4 | 0.2 | 0.7 | | | 5-10 |
| Tallow | | | 0.1 | 3.2 | 23.4 | 18.6 | 42.6 | 2.6 | 0.7 | 0.2 | 0.3 | | | 5-10 |

[1]Values measure at the Analytics lab of Neste Oyj by CG.
[2]Estimation of C16-C18 FFAs in %-wt is based on ½ * TAN (total acid number analysis), which is a fair approximation.

In addition to fatty acid glycerides, the common renewable system feed and/or the renewable process feed may comprise one or more of fatty and/or resin acids, and thermally liquefied renewable and/or recycled organic material. A non-exhaustive list of exemplary common renewable system feeds and/or renewable process feeds includes one or more of vegetable oils such as rapeseed oil, canola oil, soybean oil, coconut oil, sunflower oil, palm oil, palm kernel oil, peanut oil, linseed oil, sesame oil, maize oil, poppy seed oil, cottonseed oil, soy oil, tall oil, corn oil, castor oil, jatropha oil, jojoba oil, olive oil, flaxseed oil, camelina oil, safflower oil, babassu oil, *Brassica* species seed oil, especially *Brassica carinata* seed oil, and rice bran oil, or fractions or residues of said vegetable oils such as palm olein, palm stearin, palm fatty acid distillate (PFAD), purified tall oil, tall oil fatty acids, tall oil resin acids, tall oil unsaponifiables, tall oil pitch (TOP), and used cooking oil of vegetable origin; animal fats such as tallow, lard, yellow grease, brown grease, fish fat, poultry fat, and used cooking oil of animal origin; microbial oils, such as algal lipids, fungal lipids and bacterial lipids; and thermally liquefied renewable organic material, such as pyrolyzed, hydrothermally liquefied, and/or solvothermally liquefied solid or fluid biomass. Also thermally liquefied recycled organic materials such as pyrolyzed, hydrothermally liquefied, and/or solvothermally liquefied waste plastics, municipal waste and/or end-of-life tires, may be incorporated in the common system feed and/or in any of the renewable process feeds.

The integrated production plant system comprises a storage unit configured to receive the common renewable system feed. Sometimes also the renewable process feeds and/or renewable product flow fractions may be introduced to the storage unit. The storage unit may comprise several reservoirs e.g. for different feed materials or grades. This may be beneficial if certain feed materials are expected to react with each other e.g. causing precipitates. Such feeds could then be co-fed from the separate reservoirs to the same renewable process. Sometimes incorporating a less viscous feed into same reservoir with a different, more viscous feed material, as a mixture, may be beneficial, allowing reducing viscosity of the more viscous feed thereby improving e.g. handleability and/or water removal therefrom. Sometimes incorporating a feed with more impurities into same reservoir with a different, purer feed material, as a mixture, may be beneficial, rendering the feed material with more impurities usable in the renewable processes.

Pretreatment

The common renewable system feed and/or any of the respective renewable process feeds may be pretreated by one or more known methods, such as thermally, mechanically for instance by means of shear force, chemically for instance with acids or bases, or physically with radiation, distillation, cooling, or filtering. One of the purposes of the thermal, chemical and/or physical pretreatments is to remove impurities interfering with the processes or poisoning of catalysts, when used, and to reduce unwanted side reactions. Such pretreatments may also enhance storage stability of the renewable feeds. Hence, according to one embodiment, at least part of the common renewable system feed and/or renewable process feeds is subjected to pretreatment before entering the respective renewable process. The pretreatment may include one or more of blending, bleaching such as wet bleaching or dry bleaching, degumming such as water degumming, soft degumming or acid degumming, deodorizing, treating with an absorbent and/or adsorbent, filtering, sedimentation, decanting, centrifuging, thermal separation e.g. evaporating or distillation such as fractional distillation, heat treating, flocculating, catalytic hydrogenation of olefinic bonds. Pretreatment may involve e.g. a thermal separation method using heating and separating compounds based on their different boiling points, optionally at reduced pressure (vacuum). Such separation methods include various evaporation and distillation processes. The pretreatment may be conducted e.g. using one or more conventional pretreatment units. Some of the pretreatments, such as sedimentation and decanting, could also be done in the storage unit.

One of the benefits of having at least two plants of different kinds at one production site is that the feed base of the integrated production plant system may be broadened, as the individual plants may utilize different feeds or feed fractions having different qualities and compositions. When using any of the above mentioned pretreatments, the feed base of the integrated production plant system may be broadened even further.

(Trans)esterification

Esterification may comprise esterification of fatty or resin acids in the presence of alkyl alcohols such as a C1-C4 alkyl alcohol to yield a fatty or resin acid ester containing stream. When fatty or resin acid esters/glycerides are present in the feed (starting esters), this step comprises a transesterification of the starting esters in the presence of an alkyl alcohol such as C1-C4 alkyl alcohol to yield a stream containing the respective fatty or resin acid ester.

As used herein, references to carbon numbers of fatty or resin acid esters disregard the carbon number of the residue originating from the alcohol. For example, ethyl palmitate ($C_{18}H_{36}O_2$) is referred to as C16 fatty acid ester, or C16 fatty acid ethyl ester, hence a fatty acid ester wherein the fatty acid residue carbon chain length is C16 and the two other carbons originate from ethanol.

Transesterification is a process well known in the art, e.g. for production of biodiesel, such as FAME (fatty acid methyl ester). Glycerides are reacted in the presence of an alcohol to fatty acid esters. A common alcohol is methanol, producing fatty acid methyl esters (FAME). If ethanol is used in transesterification, fatty acid ethyl esters (FAEE) are obtained. Catalysts suitable for such reactions are known in the art. Hence, the ester bonds between glycerol and fatty acids are cleaved releasing glycerol, but the fatty acid residues are still in form of esters. The separation of glycerol from fatty acid esters formed is known in the art. An effective way of removing excess alcohols ang glycerol is extraction with water. During transesterification and downstream processing thereof, some water is accumulated to the glycerol stream. Aqueous glycerol may be further reacted to useful compounds, such as C3-alcohols, including 1-propanol, 2-propanol, 1,2-propanediol and 1,3-propanediol.

The alkyl alcohol used for (trans)esterification is preferably selected from C1-C4 alkyl alcohols hence, methanol, ethanol, 1-propanol, 2-propanol, 1-butanol and 2-butanol, or a mixture thereof, preferably from renewable alkyl alcohols. Alkyl alcohol refers to an alcohol comprising only one hydroxyl group. Renewable ethanol is abundantly available from fermentation of sugars and carbohydrates. Renewable propanols may be obtained from e.g. crude glycerol. In embodiments involving ketonisation in a renewable base oil process and metathesis with a C2-C4 alkene in a renewable chemical process, C2-C4 alcohols may be preferred for (trans)esterification providing synergistic advantages to the overall process as producing alkenes in ketonisation reactions. In embodiments involving manufacture of C3-alcohol by selective hydroprocessing of crude glycerol in a renewable chemicals process, that C3-alcohol may be preferred alkyl alcohol for (trans)esterification providing synergistic advantages to the overall process.

In one embodiment ethanol in esterification and ethene in metathesis correspondingly are used. Preferably, the ethanol is renewable. Such use is advantageous to the overall process, and increases the share of renewable products.

As a specific embodiment, the glyceride containing feedstock may be subjected to splitting, preferably hydrolysis before said esterification reaction, or just to liberate crude glycerol for manufacturing C3-alcohols therefrom. In said hydrolysis, glycerol and free fatty acids or fatty acid salts are released from mono-, di- and triglycerides. Possible fatty acid salts are converted to free acids before or during the esterification. Free fatty acids may be esterified. Combination of hydrolysis and esterification is also an alternative to transesterification. Esterification of free fatty acids is preferably catalytic, carried out over homogenous or heterogenous catalysts, such as a zinc laurate or a zinc stearate catalyst. The product obtained from (trans)esterification may be subjected to thermal separation to provide several fractions, e.g. a gas fraction comprising water and C1-04 alcohols; a fraction comprising fatty acid esters up to C16; and a fraction comprising unsaturated C18 fatty acid esters. As used herein, the thermal separation refers to any separation methods using heating and separating desired compounds based on their different boiling points. Such separation methods comprise various evaporation and distillation processes.

In a preferred embodiment, the esters obtained from (trans)esterification are subjected to fractional distillation. Said distillation provides several fractions, which may be directed to different further processing steps or collected as FAAE fuels or components thereof. In addition to fractionation, the fractional distillation contributes to purity of each fraction recovered thereby improving catalyst performance and endurance when catalytic processes are used downstream from fractional distillation.

Hydroprocessing

As used herein, term "hydroprocessing" refers to reactions in the presence of hydrogen such as one or more of hydrodeoxygenation (HDO), hydrogenation of double bonds, hydrocracking, hydroisomerisation, hydrodesulphurization, hydrodenitrification and hydrodemetallization, especially hydrodeoxygenation (HDO) and hydroisomerisation. As the common renewable system feed components and the renewable process feeds exemplified above may have relatively high oxygenate content, the hydroprocessing is needed at least for removal of covalently bound oxygen from the oxygen containing feed and in some embodiments, from oxygen containing intermediate products, such as ketones. Typically, this means deoxygenation by hydrogenation i.e. hydrodeoxygenation (HDO). Preferably, hydroprocessing comprises both hydrodeoxygenation and hydroisomerization. These may be conducted in separate stages or simultaneously in same reactor and/or catalyst bed.

Hydrodeoxygenation

Hydrodeoxygenation of oxygen containing feeds may be carried out as depicted e.g. in EP1741768A1, WO2007068795A1, WO2016062868A1 or EP2155838B1, and using a conventional hydroprocessing catalysts and hydrogen containing gas.

In one embodiment the hydrodeoxygenation takes place at reaction conditions comprising a temperature in the range from 100 to 500° C., preferably from 250 to 400° C., more preferably from 280-350° C., most preferably at temperature of 300-330° C.; and at a pressure in the range from 0.1 to 20 MPa, preferably from 0.2 to 8 MPa. Preferably, the weight hourly space velocity (WHSV) is in the range from 0.5 to 3.0 $h^{-1}$, more preferably from 1.0 to 2.5 $h^{-1}$, most preferably from 1.0 to 2.0 $h^{-1}$. Preferably, $H_2$ flow is in the range from 350 to 900 nl $H_2$/l feed, more preferably from 350 to 750, most preferably from 350 to 500, wherein nl $H_2$/l means normal liters of hydrogen per liter of the feed into the HDO reactor, in the presence of a hydrodeoxygenation catalyst. The hydrodeoxygenation catalyst is preferably selected from Pd, Pt, Ni, Co, Mo, Ru, Rh, W, or any combination of these, such as CoMo, NiMo, NiW, CoNiMo on a support, wherein the support is preferably alumina and/or silica, preferably CoMo or NiMo on alumina support.

Isomerization (Hydroisomerization)

Isomerization can be carried out e.g. in a conventional hydroisomerization unit, such as those depicted in FI100248B, EP1741768A1, WO2007068795A1, WO2016062868A1 or EP2155838B1. Hydrogen is present in the isomerization.

Both the hydrodeoxygenation step and hydroisomerization step may be conducted in the same reactor, and even in the same reactor bed. The hydroisomerization catalyst may be a noble metal bifunctional catalyst such as a Pt containing commercial catalyst, for example Pt-SAPO or Pt-ZSM-catalyst or for example a non-noble catalyst, such as NiW. The hydrodeoxygenation and hydroisomerization steps may be performed using NiW catalyst, or even in the same catalyst bed using the NiW catalyst for both the hydrodeoxygenation and isomerization. The NiW catalyst may additionally result in more hydrocracking to diesel and naphtha products.

The hydroisomerization is preferably performed at a temperature from 250 to 400° C., more preferably from 280 to 370° C., most preferably from 300 to 350° C. Pressure is preferably from 1 to 6 MPa, more preferably from 2 to 5 MPa, most preferably from 2.5 to 4.5 MPa. The WHSV is preferably from 0.5 to 3 1/h, more preferably from 0.5 to 2 1/h, most preferably from 0.5 to 1 1/h, and $H_2$ flow from 100 to 800, more preferably from 200 to 650, most preferably from 350 to 500 n-liter $H_2$/liter feed, wherein n-liter $H_2$/l means normal liters of hydrogen per liter of the feed into the isomerization reactor.

During hydroisomerization n-paraffins are branched i.e. forming i-paraffins. Preferably, the conditions are chosen such that the branches are located at or near the terminal ends of the molecules, thus improving the cold flow properties of renewable fuels and/or base oils.

Ketonization

The renewable base oil process may be based on a ketonization reaction, optionally followed by hydrodeoxygenation and isomerization. In certain embodiments, the ketonization is applied according to specific embodiments and related to processing of a fatty acid ester fraction, preferably comprising at least 80%-wt of saturated fatty acid esters having a carbon chain length of C12-C16.

The alcohol used for esterification, provides in the ketonisation reaction an alkene, that has been found to be usable in the metathesis reaction. Hence, when ethanol is reacted with fatty acids to produce esters in esterification, the ethene released during ketonisation of two of such esters can be recycled to metathesis reaction. The same applies to use of C3-alcohols, such as propanol, yielding propene from ketonisation. Preferably a single alcohol and corresponding alkene for metathesis are used at a time.

As steps, this can be described as subjecting the fraction comprising saturated fatty acid esters having carbon chain length from C12 to C16, to ketonisation and hydroprocessing to produce renewable base oil comprising C31 hydrocarbons, wherein said hydroprocessing comprises hydrodeoxygenating and isomerizing the obtained ketone stream into saturated hydrocarbon stream comprising C31 i-paraffins and n-paraffins.

Ketonisation reaction is an excellent deoxygenation reaction when deoxygenation, stability and energy density of products are the targets, as is often the case in production of base oils. Ketonisation removes 75 mol-% of the oxygen bound to carboxylic acid molecules without use of hydrogen. During the ketonisation reaction two fatty acid alkyl ester molecules are reacted together forming the corresponding linear ketone. One molecule of $CO_2$, water and two alkenes is simultaneously released during the reaction.

Ketonisation reaction may be carried out with high conversion, such as 95%, or 98%, or even 99.9%, and with excellent selectivity, such as 85%, or 92%, or even 95%, which is the reason why the renewable base oil yield can be almost theoretical. Due to the very selective ketonisation reaction only few or no light hydrocarbons are formed, therefore, $CO_2$ recovered from the ketonisation reaction can be very pure, preferably at least 99% by volume, and it can be used for varying applications. Naturally, the ketones produced from the free fatty acid fractions obtained by the process of the present invention may also be used as chemicals for various applications other than base oil or fuel component production.

In certain embodiments, a fatty acid ester fraction, comprising fatty acid esters having a carbon chain length of C12-C16 in an amount of at least 80%-wt of the total fraction weight, is subjected to ketonisation. Ketonisation product obtained from this reaction yields a product mixture that comprises C31 ketone. It is advantageous that the amount of said C31 ketone is at least 50%-wt, preferably at least 60%-wt, more preferably at least 70%-wt of the product mixture weight.

In certain embodiments, the ketonisation reaction may be carried out at a reaction temperature ranging from 300 to 400° C., more preferably from 330 to 370° C., most preferably from 340 to 360° C. The pressure range may be from from 0.5 to 3.0 MPa, more preferably from 1.0 to 2.5 MPa, most preferably from 1.5 to 2.0 MPa, in the presence of a ketonisation catalyst. A suitable ketonisation catalyst comprises one or more metal oxide catalysts, preferably the metal of the metal oxide catalyst is selected from one or more of Na, Mg, K, Sc, Fe, Co, Ni, Cu, Zn, Sr, Y, Zr, Mo, Rh, Cd, Sn, La, Pb, Bi, Ti, Mn, Mg, Ca, Zr and rare earth metals. More preferably, the ketonisation catalyst is a metal oxide catalyst selected from the list consisting of one or more of: Ti, Mn, Mg, Ca, and Zr containing metal oxide catalyst. Most preferably, the catalyst is Ti containing metal oxide catalyst, such as $K_2O/TiO_2$ catalyst, or $TiO_2$ containing catalyst, such as $TiO_2$ catalyst. The weight hourly space velocity (WHSV) may be in the range from 0.25 to 3.0 h−1, preferably from 0.5 to 2.0 h−1, more preferably from 1.0 to 1.5 h−1. Ketonisation reaction may be performed in the presence of a gas in the range from 0.1 to 1.5 gas/feed ratio (w/w), preferably from 0.25 to 1.0, most preferably from 0.5 to 0.75, wherein the gas/feed ratio (w/w) means the mass of gas fed into the ketonisation reactor per the inlet fatty acid mass of the liquid feed into the ketonisation reactor. The gas is selected from one or more of: $CO_2$, $H_2$, $N_2$, $CH_4$, $H_2O$. Use of $H_2$ as gas provides advantages when applied in processes where the next phase also requires the presence of hydrogen, such as HDO. Then $H_2$ may flow through the reactor into said next phase. The most preferred gas is $CO_2$ as this is the product gas and may be efficiently recycled back to the feed, and it provides the most selective ketonisation reaction. According to a preferred embodiment, the ketonisation reaction conditions comprise the presence of $CO_2$ gas flow, preferably $CO_2$ flow from 0.25 to 1 gas/feed (w/w). The $CO_2$ used in the ketonization reaction could be obtained from the conversion of the carbonaceous waste stream.

The alcohol used for (trans)esterification reaction, provides a corresponding alkene in the ketonisation reaction, that may be used as an alkene reagent in metathesis reaction. Hence, when ethanol is reacted with fatty acids to produce esters, the ethene released correspondingly from ketonisation of two esters can be directed to a metathesis reaction. The same applies to use of C3-alcohols, such as propanol, yielding propene from ketonisation.

Metathesis

As used herein, metathesizing is not limited to any particular type of metathesis of unsaturated/olefinic compounds, and may refer to cross-metathesis (i.e., co-metathesis), self-metathesis, ring-opening metathesis, ring-opening metathesis polymerizations, ring-closing metathesis, and acyclic diene metathesis. In some embodiments, metathesizing refers to reacting two unsaturated fatty acid alkyl esters (self-metathesis) in the presence of a metathesis catalyst, wherein each unsaturated FAAE has a carbon-carbon double bond, thereby forming a new mixture of olefins and esters which may include a dimer. Such dimers may have more than one olefinic bond, thus higher oligomers may also form. Additionally, in some other embodiments, metathesizing may refer to reacting an alkene, such as ethylene, and an unsaturated FAAE having at least one carbon-carbon double bond, thereby forming new olefinic molecules (olefinic products) as well as new ester molecules (cross-metathesis).

Metathesis reactions are based on rearrangements around C=C double bonds of two molecules of starting material(s). Good feeds for renewable chemical processes involving metathesis include seed oils, such as sunflower oil, as these are rich in unsaturated fatty acid glycerides. Metathesis may aim at producing shorter alkenes and esters from unsaturated fatty acid esters. This may be achieved e.g. by reacting the fraction comprising unsaturated C18 fatty acid esters with a short chain alkene, such as a C2-C4 alkene to obtain metathesis products comprising renewable alkenes, such as 1-decene, and fatty acid derived esters. Depending on the alkene used, the length of the unsaturated fatty acids and the double bond position therein, a metathesis reaction between these components produces a mixture comprising C5-C12 alkenes and C6-C18 unsaturated esters. Saturated compounds, such as alkyl stearates (C18:0 esters), act as inerts and pass through metathesis reaction unreacted.

A feed of free fatty acids may be harmful considering metathesis catalyst's lifetime or activity, therefor it is beneficial to use fatty acid alkyl esters and/or fatty acid glycerides in the renewable process feed for the renewable chemical process involving metathesis.

Advantageously, if a feed of free fatty acids is available, it is esterified before feeding into a renewable chemical process involving metathesis.

Metathesis may be conducted at a temperature from 20 to 120° C., a pressure from 0.1 to 3 MPa using at least one metathesis catalyst. The metathesis reaction can be catalyzed by one or more metathesis catalysts known in the art. Typically, fatty ester metathesis catalysts are homogeneous. In case they can catalyze side reactions in successive reaction steps, it is advantageous to remove them from the solution after metathesis.

It is considered especially advantageous to use renewable C2-C4 alkene as reagent for metathesis reaction. According to a specific embodiment, this is possible through a combination of a metathesis reaction with a ketonisation reaction releasing renewable alkenes in the same integrated method. Accordingly, according to a preferred embodiment, alkenes recovered from a ketonisation reaction of C16 fatty acid ethyl esters are directed to the metathesis reaction.

From the metathesis reaction, at least one renewable alkene and at least one fatty acid derived ester may be recovered as products. Regarding the desired products, palm oil or palm oil fatty acids provide especially advantageous feed. PFAD is especially rich in oleic acid, and is preferably used as esterified. Metathesis reaction between oleic acid ethyl ester and ethene produces 1-decene and ethyl-9-decenoate. Of these, 1-decene is especially attractive as a component for poly alpha olefin (PAO) production which again may be used for lubricant manufacture. Among other unsaturated C10-C15 fatty acid esters, ethyl-9-decenoate is an interesting precursor chemical for refining into oleo chemicals. Additionally, ethyl-9-decenoate, as well as other terminal olefins obtainable by renewable chemical processes involving metathesis, is suitable for use as a monomer in free radical polymerization, e.g. when manufacturing renewable polymers.

After the metathesis reaction, desired metathesis products may be separated from the metathesis effluent e.g. by evaporation, such as flash separation, and/or distillation, such as fractional distillation. The removed lights, such as C2-C4 alkenes, may optionally be recycled back to metathesis reaction. Separation of lights depleted metathesis effluent may be conducted by product distillation, where alkenes are recoverable. C5-C7 alkenes may be directed e.g. to renewable naphtha production. As main product fractions, 1-decene and shortened esters, such as 9-DAEE may be recovered from said product distillation.

Renewable Products

Several renewable products may be recovered from the present method. Exemplary renewable products obtainable by the present method include renewable liquid fuels, such as renewable gasoline, renewable kerosene, renewable jet fuel, renewable diesel, renewable bunker fuel, renewable heating oil, including components thereof; renewable base oils, including components thereof; or renewable chemicals, such as renewable alkanes, alkenes, terminal olefins, e.g. terminal olefinic esters, alcohols, aldehydes, acids, diacids, solvents, fatty acids, fatty alcohols, glycerine, soaps, dimer acids, esters, olefinic diesters, amides, amines, sulfonates. Such products may be used as such or in blends providing products fulfilling specifications set for said products.

The present method and integrated production plant system is especially beneficial as allowing manufacture of separate fuels, base oils or chemical products, including components thereof, but also fuel blends, base oil blends, and chemicals blends, e.g. fuels blends containing FAAE and paraffinic fuel, and lubricating compositions of FAAE and paraffinic solvent, at the same production site. Additionally, the renewable chemical processes may produce chemicals usable as additives for fuel compositions.

Transport System (Material Flow Connection)

The common renewable system feed, renewable process feeds, renewable products and waste streams are all in fluid form under the processing conditions allowing their transportation e.g. via pipelines. The transport system provides a material flow connection between the processes, the storage unit for the common renewable system feed and the optional waste processing system and pretreatment unit(s), allowing directing common system feed from the storage unit, and/or renewable process feeds, to the renewable processes, optionally after pretreatment, directing renewable products or their fractions to other renewable processes for use as feed therein, or to the common system feed unit, directing renewable process feed of one process to another process, etc. Although the transport system preferably comprises pipelines, in embodiments also trucks or other means may be used for some of the required transportation.

Without limiting the scope and interpretation of the patent claims, certain technical effects of one or more of the example embodiments disclosed herein are listed in the following. A technical effect is producing renewable fuels, base oils and/or chemicals in a flexible manner. A further technical effect is minimizing waste by the use of feedstock in an effective manner. Furthermore, side-products or residues of some of the renewable processes may be used as the process feed or additional reagents in some other renewable processes of the integrated production plant system. Such side-products or residues might be useless waste in a renewable production plant if operated separately, and not as part of the integrated production plant.

The foregoing description has provided by way of non-limiting examples of particular implementations and embodiments of the invention a full and informative description of the best mode presently contemplated by the inventors for carrying out the invention. It is however clear to a person skilled in the art that the invention is not restricted to details of the embodiments presented above, but that it can be implemented in other embodiments using equivalent means without deviating from the characteristics of the invention.

Furthermore, some of the features of the above-disclosed embodiments of this invention may be used to advantage without the corresponding use of other features. As such, the foregoing description should be considered as merely illustrative of the principles of the present invention, and not in limitation thereof. Hence, the scope of the invention is only restricted by the appended patent claims.

The invention claimed is:
1. A method, comprising:
operating an integrated production plant system including, at one production site:
at least two plants of different kinds, each providing a renewable process and being selected from:
a) a renewable paraffinic fuel plant to produce a renewable paraffinic fuel as a main product in a renewable paraffinic fuel process,
b) a renewable fatty acid alkyl ester (FAAE) fuel plant to produce a renewable FAAE fuel as a main product in a renewable FAAE fuel process,
c) a renewable base oil plant to produce a renewable base oil as a main product in a renewable base oil process, and
d) a renewable chemical plant to produce a renewable chemical as a main product in a renewable chemical process; and
a storage unit for a common renewable system feed;
providing each of the renewable processes with a respective renewable process feed, wherein at least part of each respective renewable process feed originates from the common renewable system feed;
processing each respective renewable process feed in each renewable process to obtain a respective renewable product flow;
altering i) a respective renewable process feed to at least one of the renewable processes by directing at least part of a respective renewable process feed of at least one other of the renewable processes to said at least one of the renewable processes and/or ii) the renewable product flow of at least one of the renewable processes by directing at least part of the renewable product flow of at least one other of the renewable processes to said at least one of the renewable processes for use as at least part of the respective renewable process feed.

2. The method of claim 1, wherein the common renewable system feed and/or any one or more of the renewable process feeds comprise:
at least one or more of:
one or more of fatty and/or resin acids, fatty acid glycerides, and thermally liquefied renewable and/or recycled organic material.

3. The method of claim 1, wherein the common renewable system feed and/or any one or more of the renewable process feeds comprise:
at least one or more of:
one or more of vegetable oils, including but not limited to rapeseed oil, canola oil, soybean oil, coconut oil, sunflower oil, palm oil, palm kernel oil, peanut oil, linseed oil, sesame oil, maize oil, poppy seed oil, cottonseed oil, soy oil, tall oil, corn oil, castor oil, jatropha oil, jojoba oil, olive oil, flaxseed oil, camelina oil, safflower oil, babassu oil, *Brassica* species seed oil, *Brassica carinata* seed oil, and rice bran oil, or fractions or residues of said vegetable oils including but not limited to palm olein, palm stearin, palm fatty acid distillate (PFAD), purified tall oil, tall oil fatty acids, tall oil resin acids, tall oil unsaponifiables, tall oil pitch (TOP), and used cooking oil of vegetable origin; animal fats including but not limited to tallow, lard, yellow grease, brown grease, fish fat, poultry fat, and used cooking oil of animal origin; microbial oils, including but not limited to algal lipids, fungal lipids and bacterial lipids; and thermally liquefied renewable organic material, including but not limited to pyrolyzed, hydrothermally liquefied, and/or solvothermally liquefied solid or fluid biomass.

4. The method of claim 1, wherein the integrated production plant system comprises:
at least one renewable paraffinic fuel plant and at least one renewable FAAE fuel plant; or
at least one renewable paraffinic fuel plant and at least one renewable chemical plant; or
at least one renewable paraffinic fuel plant, at least one renewable FAAE fuel plant and at least one renewable chemical plant; or
at least one renewable paraffinic fuel plant, and at least one renewable base oil plant; or
at least one renewable paraffinic fuel plant, at least one renewable base oil plant, and at least one renewable FAAE fuel plant; or
at least one renewable paraffinic fuel plant, at least one renewable base oil plant, and at least one renewable chemical plant; or
at least one renewable paraffinic fuel plant, at least one renewable base oil plant, at least one renewable FAAE fuel plant, and at least one renewable chemical plant.

5. The method of claim 1, wherein the renewable paraffinic fuel process of the renewable paraffinic fuel plant comprises:
hydroprocessing the renewable process feed; and
fractionating a hydroprocessing effluent to obtain renewable paraffinic fuel as a main product, including but not limited to renewable diesel, kerosene, gasoline and/or naphtha, diesel range paraffinic hydrocarbons meeting EN 590 requirements for automotive diesel fuel and/or kerosene range paraffinic hydrocarbons meeting ASTM D7566-16b, Annex A2, requirements for aviation turbine fuel.

6. The method of claim 1, wherein the renewable FAAE fuel process of the renewable FAAE fuel plant comprises:
(trans)esterifying a renewable process feed containing fatty acids and/or fatty acid glycerides in a presence of an alkyl alcohol, including but not limited to C1-C4 alkyl alcohol; and
fractionating a (trans)esterification effluent to obtain renewable FAAE fuel as a main product, including but not limited to biodiesel, bunker fuel, heating oil, and/or lubricant component, and/or a biodiesel fuel blend stock meeting ASTM D6751-19 standard specification for biodiesel fuel blend stock (B100) for middle distillate fuels.

7. The method of claim 1, wherein the renewable chemical process of the renewable chemical plant comprises:
metathesizing a renewable process feed containing unsaturated fatty acid glycerides and/or unsaturated fatty acid alkyl esters optionally in a presence of an olefin, and fractionating a metathesis effluent to obtain renewable chemicals as a main product, including but not limited to terminal olefin products; or
subjecting a renewable chemical process feed of crude glycerol to selective hydroprocessing to obtain renewable C3-alcohol, including but not limited to 1-propanol, 2-propanol, 1,2-propanediol or 1,3-propanediol.

8. The method of claim 1, wherein the renewable base oil process of the renewable base oil plant comprises:
ketonizing a renewable process feed containing fatty acids, fatty acid glycerides and/or FAAE; and
optionally hydroprocessing, and fractionating the ketonization and/or hydroprocessing effluent to obtain renewable base oil as a main product, including but not limited to a product meeting API group III specifications for base oils.

9. The method of claim 1, comprising:
altering both i) the renewable process feed and ii) the renewable product flow.

10. The method of claim 1, comprising:
performing the altering is based on one, two or more parameters selected from: inoperability of any of the processes, a target value for an amount of generated carbonaceous waste, a target value for an amount of generated carbon oxide(s), reduced efficiency of a solid catalyst used for processing the renewable process feed in at least one of the processes, increased pressure drop over a fixed catalyst bed used for processing the renewable process feed in at least one of the processes, predetermined target specification for any of the renewable products, predetermined target specification for any of the renewable process feeds, composition of the common renewable system feed, 14C content of the common renewable system feed and/or any of the renewable process feeds and/or renewable products, market price of the renewable products, and/or market demand of the renewable products.

11. The method of claim 1, wherein the integrated production plant system includes at least a renewable paraffinic fuel plant, a renewable chemical plant and a renewable FAAE fuel plant, and in a case where the renewable chemical process of the renewable chemical plant is not running, the method comprises:
directing a renewable product flow fraction containing unsaturated FAAE, and/or a C18-FAAE of the renewable FAAE fuel process, being used as the renewable process feed for the renewable chemical process, to the renewable paraffinic fuel process for use as renewable process feed therein, and/or collecting said renewable product flow fraction as an unsaturated FAAE fuel, and/or as a winter grade FAAE fuel.

12. The method of claim 1, wherein the integrated production plant system includes at least a renewable paraffinic fuel plant, a renewable base oil plant and a renewable FAAE fuel plant, and in a case where the renewable base oil process of the renewable base oil plant is not running the method comprises:
directing a renewable product flow fraction containing C16-FAAE of the renewable FAAE fuel process, being used as the renewable process feed for the renewable base oil process, to the renewable paraffinic fuel process for use as renewable process feed therein, and/or collecting said renewable product flow fraction as a FAAE fuel, and/or as a marine grade FAAE fuel.

13. The method of claim 1, wherein the method comprises:
blending at least part of the renewable paraffinic fuel containing diesel range paraffinic hydrocarbons, and at least part of the renewable FAAE fuel, containing a biodiesel fuel blend stock, and optionally petroleum-based hydrocarbons of diesel range, to obtain a fuel blend meeting requirements of ASTM D396-19 specification for fuel oil, or the requirements of ASTM D7467-19 specification for diesel fuel oil.

14. The method of claim 1, wherein the method further comprises a waste processing system in the integrated production plant system, and the method comprises:
passing a carbonaceous waste stream of the integrated production plant system to the waste processing system, and converting it to a conversion effluent containing carbon oxide(s).

15. The method of claim 14, wherein said converting comprises:
one or more of burning in a flaring unit, burning in a power generation unit, gasifying in a gasification unit, and reforming in a reforming unit, to obtain a conversion effluent containing carbon oxide(s), and/or carbon oxide(s) and hydrogen.

16. The method of claim 1, wherein the system includes one or more pretreatment units in the integrated production plant system, and the method comprising:
pretreating at least part of the renewable common system feed and/or of any of the renewable process feeds by at least one or more of blending, bleaching, degumming, deodorizing, filtering, sedimentation, decanting, centrifuging, evaporating, distillation, heat treating, flocculating, catalytic hydrogenation of unsaturated bonds, treating with an absorbent, and/or treating with an adsorbent.

17. An integrated production plant system comprising, at one production site:
at least two plants of different kinds selected from:
a) a renewable paraffinic fuel plant configured to produce a renewable paraffinic fuel as a main product in a renewable paraffinic fuel process,
b) a renewable FAAE fuel plant configured to produce a renewable FAAE fuel as a main product in a renewable FAAE fuel process,
c) a renewable base oil plant configured to produce a renewable base oil as a main product in a renewable base oil process, and
d) a renewable chemical plant configured to produce a renewable chemical as a main product in a renewable chemical process; and
a storage unit configured to receive a common renewable system feed;
wherein the integrated production plant system is configured to:
provide each of the processes with a respective renewable process feed, wherein at least part of each respective renewable process feed originates from the common renewable system feed;
process each respective renewable process feed in each renewable process to obtain respective renewable product flows;

alter i) a respective renewable process feed to at least one of the renewable processes by directing at least part of the respective renewable process feed of at least one other of the renewable processes to another of said at least one of the renewable processes and/or ii) a respective renewable product flow of at least one of the renewable processes by directing at least part of the renewable product flow of at least one other of the renewable processes to said at least one of the renewable processes for use as at least part of the respective renewable process feed.

18. The integrated production plant system of claim 17, comprising:
a waste processing system configured to convert a carbonaceous waste stream to a conversion effluent containing carbon oxide(s), wherein the integrated production plant system is configured to pass a carbonaceous waste stream of the integrated production plant system to the waste processing system, and to convert it to a conversion effluent containing carbon oxide(s).

19. The integrated production plant system of claim 18, wherein the waste processing system comprises:
one or more of a flaring unit, a power generation unit, a gasification unit, and a reforming unit including, but not limited to a steam reforming unit and/or a catalytic reforming unit.

20. The integrated production plant system of claim 18, comprising:
one or more pretreatment units configured to pretreat at least part of the renewable common system feed and/or of any of the renewable process feeds by at least one or more of blending, bleaching, degumming, deodorizing, filtering, sedimentation, decanting, centrifuging, evaporating, distillation, heat treating, flocculating, catalytic hydrogenation of unsaturated bonds, treating with an absorbent, and/or treating with an adsorbent.

21. The integrated production plant system of claim 20, comprising:
material flow connections, including pipelines, to provide for fluid communication between the plants, the storage unit, and the waste processing system and pretreatment unit(s).

22. A control system for an integrated production plant system of claim 17, comprising:
at least one processor;
at least one memory containing program code executable by the at least one processor; and
at least one communication unit configured to communicate with process flow or product flow adjustment unit(s) of the integrated production plant system to control the other of the respective renewable process feed, and/or the respective renewable product flow.

* * * * *